(12) United States Patent
Laakkonen et al.

(10) Patent No.: US 8,188,221 B2
(45) Date of Patent: May 29, 2012

(54) PEPTIDE HOMING TO BRAIN TUMORS

(75) Inventors: Pirjo Laakkonen, Helsinki (FI); Erkki Ruoslahti, La Jolla, CA (US); Gabriele Bergers, San Francisco, CA (US)

(73) Assignees: Burnham Institute for Medical Research, La Jolla, CA (US); The Regents of the University of California, UCSF, San Francisco, CA (US)

( * ) Notice: Subject to any disclaimer, the term of this patent is extended or adjusted under 35 U.S.C. 154(b) by 0 days.

(21) Appl. No.: 12/991,755

(22) PCT Filed: May 8, 2009

(86) PCT No.: PCT/FI2009/050375
§ 371 (c)(1),
(2), (4) Date: Jan. 28, 2011

(87) PCT Pub. No.: WO2009/136007
PCT Pub. Date: Nov. 12, 2009

(65) Prior Publication Data
US 2011/0130342 A1   Jun. 2, 2011

Related U.S. Application Data

(60) Provisional application No. 61/071,644, filed on May 9, 2008.

(30) Foreign Application Priority Data

May 9, 2008  (FI) ..................................... 20085427

(51) Int. Cl.
*C07K 16/00*  (2006.01)
(52) U.S. Cl. ........................................ 530/328; 514/19.3
(58) Field of Classification Search .................. None
See application file for complete search history.

(56) References Cited

U.S. PATENT DOCUMENTS

| 6,576,239 | B1 | 6/2003 | Ruoslahti et al. |
| 2004/0087499 | A1 | 5/2004 | Laakkonen et al. |
| 2006/0160743 | A1 | 7/2006 | Zhang et al. |

FOREIGN PATENT DOCUMENTS

| WO | 97/10507 A1 | 3/1997 |
| WO | 00/42973 A2 | 7/2000 |
| WO | 02/069885 A2 | 9/2002 |
| WO | 03/066663 A2 | 8/2003 |
| WO | 2007/090194 A2 | 8/2007 |
| WO | 2008/063113 A1 | 5/2008 |

OTHER PUBLICATIONS

Enbäck et al., "Tumour-homing peptides: tools for targeting, imaging and destruction," Biochemical Society Transactions, 2007, vol. 35, Part 4, pp. 780-783.
Finnish Search Report dated Feb. 4, 2009 for corresponding Finish Application No. 20085427.
International Search Report dated Jul. 28, 2009 for corresponding International Application No. PCT/FI2009/050375.
Laakkonen et al., "Antitumor activity of a homing peptide that targets tumor lymphatics and tumor cells," Proceedings of the National Academy of Sciences of the United States of America, Jun. 22, 2004, vol. 101, No. 25, pp. 9381-9386.
Pilch et al., "Peptides selected for binding to clotted plasma accumulate in tumor stroma and wounds," Proceedings of the National Academy of Sciences of the United States of American, Feb. 21, 2006, vol. 103, No. 8, pp. 2800-2804.

*Primary Examiner* — Sheela J Huff
(74) *Attorney, Agent, or Firm* — Birch, Stewart, Kolasch & Birch LLP

(57) ABSTRACT

The present invention relates to a peptide, which specifically homes to the intracranial, early stage astrocytoma model that grows as islets and harbors co-opted tumor vessels in the brain. The peptide finds its use in targeted delivery of therapeutic substances to invasive brain cancer or metastatic brain lesions as such and in combination with conventional therapies, such as surgery and radiation, and anti-angiogenic therapies, and as a tool in diagnosis of, e.g., invasive brain cancer or metastatic brain lesions.

7 Claims, 6 Drawing Sheets

SEQUENCE LISTING

<160> NUMBER OF SEQ ID NOS: 1

<210> SEQ ID NO 1
<211> LENGTH: 9
<212> TYPE: PRT
<213> ORGANISM: Artificial sequence
<220> FEATURE:
<223> OTHER INFORMATION: Brain homing peptide

<400> SEQUENCE: 1

Cys Gly Leu Ser Gly Leu Gly Val Ala
1               5

PEPTIDE HOMING TO BRAIN TUMORS

This application is the National Phase of PCT/FI2009/050375 filed on May 8, 2009, which claims priority under 35 U.S.C. 119(e) to U.S. Provisional Application No. 61/071,644 filed on May 9, 2008, and under 35 U.S.C. 119(a) to Patent Application No. 20085427 filed in Finland on May 9, 2008, all of which are hereby expressly incorporated by reference into the present application.

FIELD OF THE INVENTION

The present invention relates to a peptide, which specifically homes to the intracranial, early stage astrocytoma model that grows as islets and harbors co-opted tumor vessels in the brain, and to different glioma models. The peptide is useful in targeted delivery of therapeutic substances to brain tumors as such and in combination with conventional therapies, such as surgery and radiation, and anti-angiogenic therapies. This peptide may also be used as an effective tool in diagnosis of, e.g., invasive brain cancers and metastatic lesions of other tumor types in the brain.

BACKGROUND OF THE INVENTION

Astrocytes arise from multipotent neural stem cells and retain their capacity for division throughout their life span. This property is likely to make them susceptible for transformation and to contribute to the fact that astrocyte-derived tumors are the most common brain tumors in adults. Low-grade astrocytomas acquire their blood supply by propagating along the existing normal blood vessels in a process termed vessel cooption (Holash et al., 1999; Kim et al., 2002). This leads to diffuse invasion of tumor cells over long distances in the brain without formation of real tumor masses. As grade III astrocytomas progress to grade IV astrocytomas they grow in size, and to cope with the increased need for nutrients and oxygen they undergo an angiogenic switch. These most malignant forms of astrocytomas, glioblastoma multiforme, become highly vascularised and tumors appear more local than the low-grade astrocytomas. Unlike angiogenic tumor vasculature, which has been one of the main focuses of cancer research during last years, the biology of the co-opted vascular beds is poorly understood.

The prognosis for patients suffering from brain tumors is poor and has not improved during the last decades. Especially low-grade astrocytomas are challenging because they have shown to be unreachable by conventional treatment strategies such as radiation or surgery. Furthermore, they would remain in the brain after anti-angiogenic therapies. The inhibition of tumor angiogenesis has proven to be an efficient therapeutic strategy to treat a variety of malignant tumors. However, systemic anti-angiogenic treatment of malignant brain tumors seemed to lead to an increased number of satellite tumors in experimental animal models and might even encourage tumor cells to a more invasive phenotype (Kunkel et al., 2001; Rubenstein et al., 2000). Therefore, new therapies are urgently needed to prolong the survival of patients suffering from these extremely aggressive tumors.

Recently it has become apparent that each tissue expresses its own specific set of cell surface proteins on vascular endothelial cells. In addition, many pathological conditions including tumors, diabetes, atherosclerosis and inflammatory diseases, add their disease-specific tags to the endothelium of the affected tissues. In vivo biopanning using phage displayed peptide libraries is a powerful tool to profile this vascular heterogeneity and map regional and disease-specific differences in the vasculature.

By using this technology, we have isolated several peptides homing specifically to the tumor vasculature (Laakkonen and Ruoslahti, 2006; Ruoslahti, 2002). We have also shown that the vasculature of a pre-malignant lesion differs from that of a full-blown tumor and from the vasculature of the corresponding normal organ (Hoffman et al., 2003; Joyce et al., 2003). Some of the tumor-homing peptides recognize common angiogenesis markers and are capable of homing to several types of tumors while other peptides recognize tumor-type specific differences. Recently, we have isolated peptides with novel homing specificities, for example peptides that home to tumor lymphatic vessels (Zhang et al. 2006; Laakkonen et al. 2004; Laakkonen et al. 2002).

SUMMARY OF THE INVENTION

The present invention discloses a novel, nine amino acid long peptide CGLSGLGVA, as set forth in SEQ ID NO: 1. The peptide was identified using an ex vivo/in vivo phage display screen described by Hoffman et al. (2004) when screening for astrocytoma/glioblastoma stage-specific markers. The CGLSGLGVA peptide very specifically homes to the astrocytoma islets harboring co-opted tumor blood vessels in the mouse model of astrocytoma (early phase of glioblastoma).

Consequently, a primary object of the present invention is to provide a peptide comprising the amino acid sequence CGLSGLGVA (SEQ ID NO:1). A preferable embodiment is the peptide CGLSGLGVA itself.

Another object of the invention is to provide a composition comprising a peptide which comprises the amino acid sequence CGLSGLGVA, and at least one carrier and/or diluent.

A further object of the invention is a pharmaceutical composition comprising a pharmaceutically active agent in association with the peptide of the invention and at least one pharmaceutically acceptable carrier and/or diluent.

A still further object of the invention is a diagnostic or imaging composition comprising a peptide which comprises the amino acid sequence CGLSGLGVA, and a detectable label.

Another object of the invention is a method for targeted therapy of invasive brain cancers and metastatic lesions of the brain, in which method an efficacious amount of a pharmaceutical composition of the invention is administered to a patient in need of such therapy.

Still another object of the invention is a diagnostic method for diagnosing an invasive brain cancer or a metastatic brain lesion in a patient. The method comprises the steps of conjugating the peptide of the invention to a detectable label, administering the labeled peptide to the patient, and detecting the label.

The peptide according to the invention is useful at least in diagnosing invasive brain cancers or metastatic brain lesions, and in targeting pharmaceutically active agents to these sites.

DETAILED DESCRIPTION OF THE INVENTION

Figure 1:
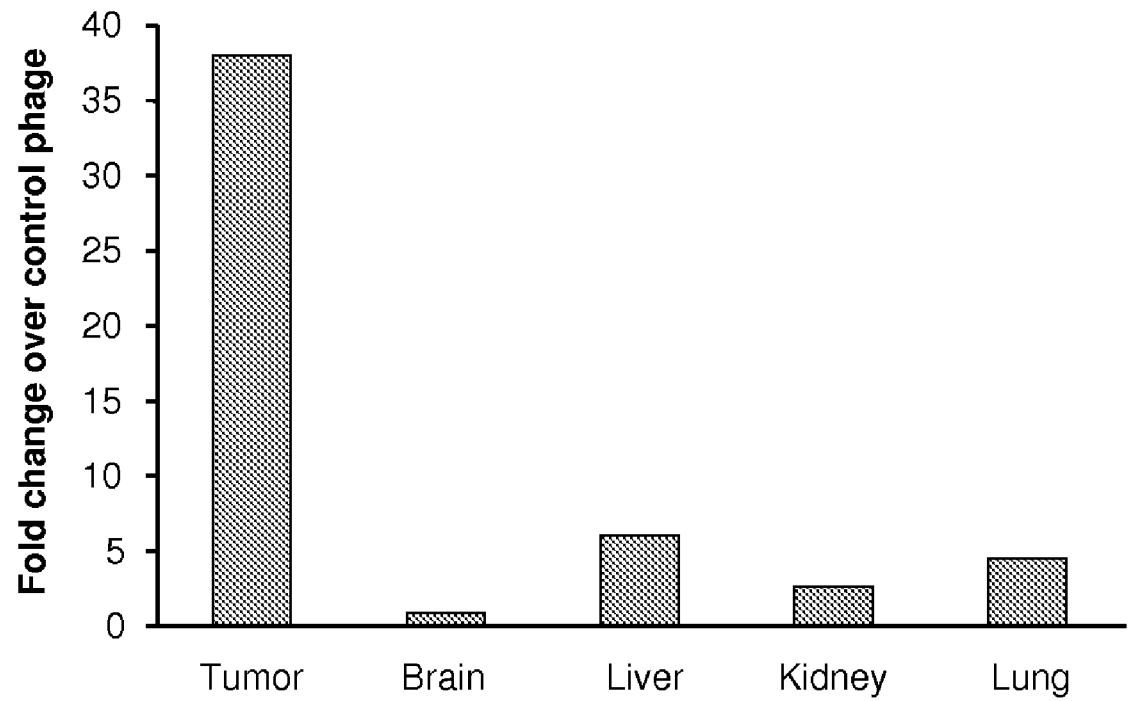
FIG. 1. Homing of the phage displaying peptide sequence CGLSGLGVA to the intracranial islet tumors.

For this invention we have used an ex vivo/in vivo phage display screen described by Hoffman et al., 2004 to identify astrocytoma/glioblastoma stage-specific markers. Briefly, HIFko astrocytes (Blouw et al., 2003) were injected intracranially into atymic, immuno-compromised mice. Tumors were allowed to establish for 9-11 days before the start of the experiments. CX7C peptide library displayed on the T7 phage was incubated with cell suspension prepared from a tumor containing brain over night followed by the rescue and amplification of the bound phage. This ex vivo step was repeated with the amplified phage pool to enrich peptides that bound to all the cells in the tumor. The enriched phage pool was then injected into the tail vein of brain tumor bearing mice and allowed to circulate for 15 min. Unbound phage was removed by saline perfusion through the heart and the bound phage was rescued and amplified. This in vivo panning step was repeated twice to enrich peptides that were able to home to tumors via blood circulation. We sequenced the peptide insert from 50 individual phages representing the third in vivo round. We tested the tumor specificity of various peptides that were enriched in the sequenced pool.

We thus identified a novel, nine amino acid long peptide (CGLSGLGVA) that very specifically homes to the intracranial, early stage astrocytoma model that grows as islets and harbors co-opted tumor vessels in the brain, and to different glioma models.

Homing of this peptide to the tumor tissue was verified by histological analysis of fluorescein-conjugated synthetic peptide. Our results show that this peptide does not recognize the angiogenic VEGF overexpressing astrocytoma tumors or normal brain, nor does it home to the early astrocytoma model (HIFko) when grown subcutaneously. In addition, the peptide of the invention homes to the U87MG human glioblastoma xenografts. Interestingly, the homing pattern of the peptide in U87MG xenografts differs from that in the astrocytoma xenografts; peptide distribution resembled that of a blood vascular endothelial cell marker after intravenous injection into the tail vein of U87MG tumor-bearing mice, while in the islet tumor model (HIFko) the peptide was detected diffusively throughout the tumor tissue.

However, the peptide did not exactly colocalize with the endothelial marker PECAM-1 but was detected close to the endothelium suggesting that the peptide had already transferred into the tumor tissue since tissues were collected 15-60 min post-injection for the histological analysis. This peptide is a very promising candidate to be used in targeted delivery of therapies to the brain tumors as such and in combination with conventional therapies, such as surgery and radiation, and anti-angiogenic therapies.

For the purposes of this invention the expression "in combination with conventional therapies" is supposed to cover not only simultaneous, but also consecutive therapies.

Anti-angiogenic therapies are known to a man skilled in the art. Any such therapy may be combined to the therapy practiced with the pharmaceutical composition of the invention.

The pharmaceutically active agent in the pharmaceutical composition of the invention is, e.g., a pro-apoptotic peptide or a chemotherapeutic or radiotherapeutic agent, which can be used for targeted therapy in invasive brain tumor or metastatic brain lesion carrying patients. Any pro-apoptotic peptide known in the art for this purpose may be used for the pharmaceutical compositions of the invention. Likewise, any chemotherapeutic or radio-therapeutic agent known in the art may be used in the present invention, and it is within the expertise of a man skilled the art to select suitable chemo- or radiotherapeutics. Determining the amounts and concentrations of the pharmaceutically active agents used in the compositions of the present invention are within the skills of those familiar with the art.

The peptide of the invention may be prepared using conventional methods, for instance chemical synthesis, and will result in a peptide powder. The peptide will then be solubilized in $H_2O$, saline or a pharmaceutically acceptable organic solvent to be injected intravenously to a patient.

Preparation of the composition of the invention is carried out by chemical conjugation of the carrier or diluent to the peptide of the invention and will result in a powder, which may be solubilized in $H_2O$, saline or an organic solvent. To prepare a pharmaceutical composition a pharmaceutically acceptable carrier or diluent is conjugated to the peptide of the invention, and a solution of the pharmaceutically active agent is added to the conjugate. The solution as obtained will be suitable to be injected intravenously to a patient. Preferably, the solution is sterile.

The concentrations of the peptide of the invention in a pharmaceutical composition may vary in wide ranges. It should be noted that the optimal concentration and the actual amounts used usually vary depending on, e.g., the clinical state of the patient to be treated.

The preferable route of administration of the peptide or the pharmaceutical composition of the invention is intravenous administration.

The pharmaceutical composition of the present invention can be administered to any animal that can experience the beneficial effects of such a composition. Human beings are foremost among such animals, although the invention is not intended to be limited to the medical treatment or diagnosis of human beings.

EXPERIMENTAL

Example 1

Homing of the Phage Displaying Peptide Sequence CGLSGLGVA to the Intracranial Islet Tumors CGLSGLGVA or a control phage ($10^9$ pfu=plaque forming unit) were injected into the tail vein of intracranial HIF-1alfa KO (HIFko) tumor-bearing mice. After 15 min of circulation the mice were perfused through the heart with saline to remove unbound phage followed by excision of tumor containing brain, normal brain, liver, kidney and lungs. The number of phage homed to those organs were determined by titration. FIG. 1 shows as a bar graph that the peptide very specifically homes to the intracranial, early stage astrocytoma model (HIFko) that grows as islets and harbors co-opted tumor vessels in the brain.

Example 2

Figure 2:
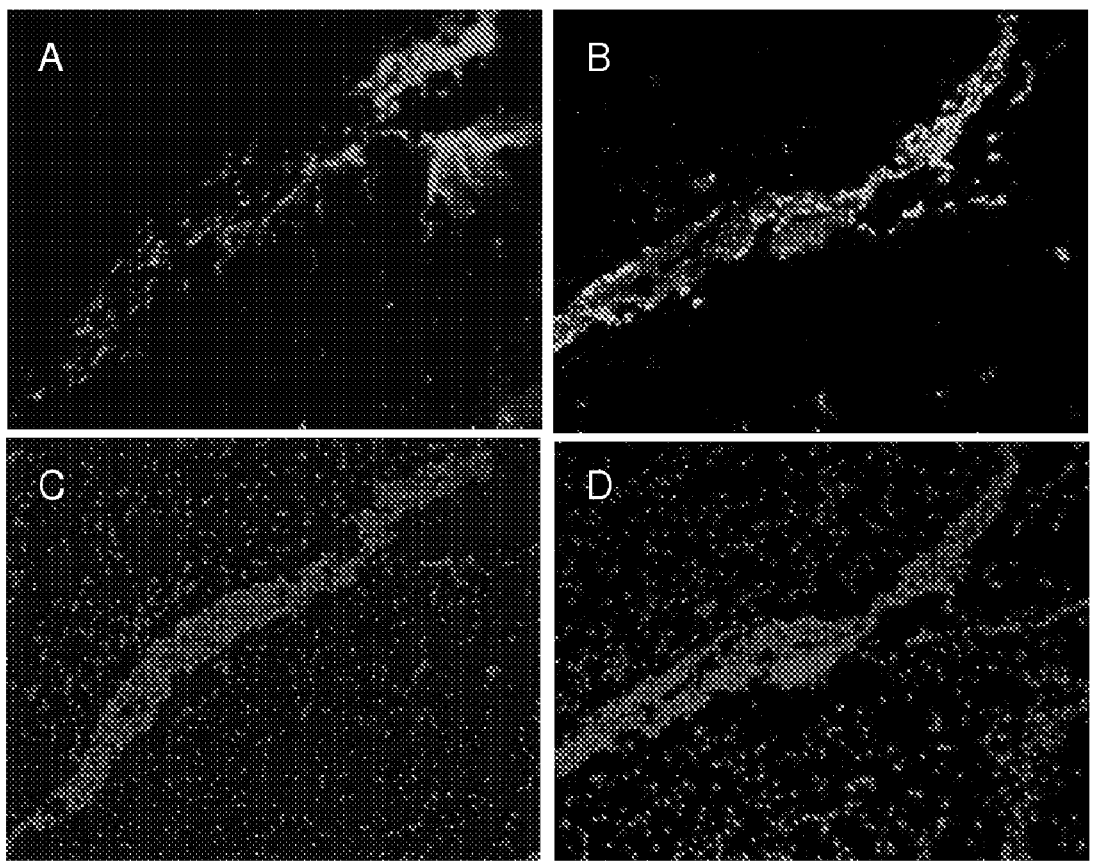
FIG. 2. (A to D) Homing of the fluorescein-conjugated CGLSGLGVA peptide to the intracranial islet tumors.

Homing of the Fluorescein-Conjugated CGLSGLGVA Peptide to the Intracranial Islet Tumors Fluorescein-conjugated CGLSGLGVA peptide (10 µg) was injected into tail vein of HIFko tumor-bearing mice. After 60 min of circulation tumor-containing brain was excised and prepared for histological analysis. Peptide was visualized by using an antibody against fluorescein (rabbit anti-FITC, Zymed Laboratories). FIG. 2 shows that the peptide (red in FIG. 2A) was detected only in the tumor islets and not in the surrounding normal brain tissue. Presence of the tumor cells was confirmed by staining for the SV40 T-antigen specific for tumor cells from a subsequent section (green in FIG. 2B). FIGS. 2C and 2D show the same microscopic field as 2A and 2B. Nuclei were visualized by DAPI staining (blue).

Example 3

Figure 3:
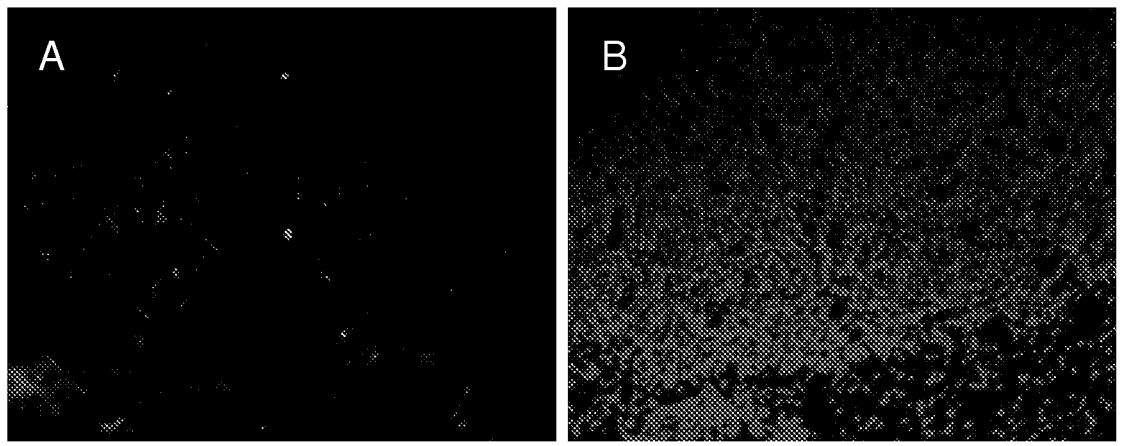
FIG. 3. (A and B) Fluorescein-conjugated CGLSGLGVA peptide does not home to the intracranial VEGF-overexpressing tumors.

Fluorescein-Conjugated CGLSGLGVA Peptide Does Not Home to the Intracranial VEGF-Overexpressing Tumors Fluorescein-conjugated CGLSGLGVA peptide (10 μg) was injected into the tail vein of VEGF overexpressing (VEGF+) tumor-bearing mice. After 60 min of circulation tumor was excised and prepared for histological analysis. Peptide was visualized by using an antibody against fluorescein (rabbit anti-FITC, Zymed Laboratories). FIG. 3A. Peptide was not detected in the tumor tissue. 3B: Same microscopic field as in 3A. Nuclei were visualized by DAPI staining (blue).

Example 4

Figure 4:
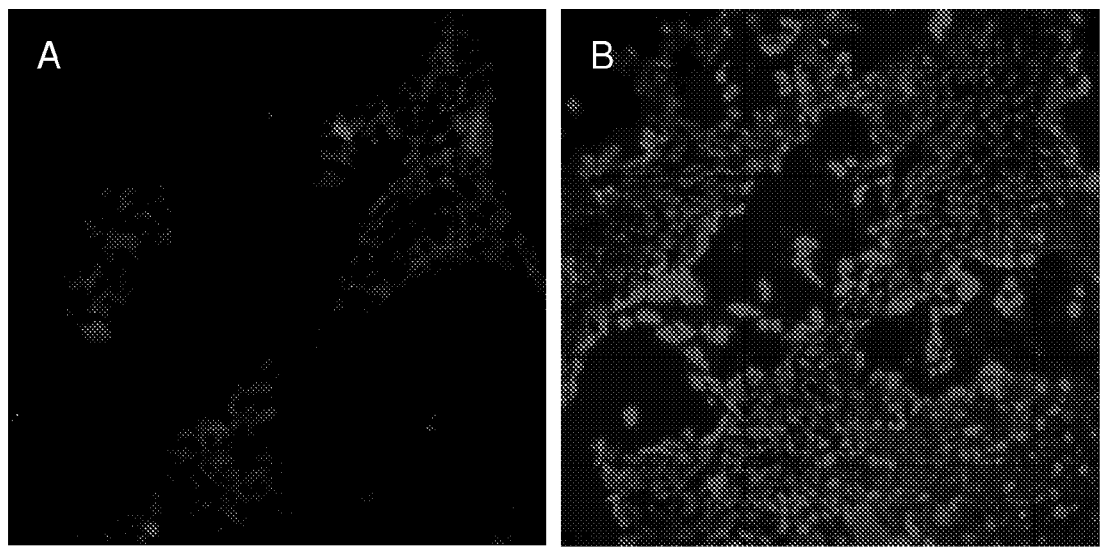
FIG. 4. (A and B) Fluorescein-conjugated CGLSGLGVA peptide does not home to the subcutaneous HIFko tumors.

Fluorescein-Conjugated CGLSGLGVA Peptide does not Home to the Subcutaneous HIFko Tumors Fluorescein-conjugated CGLSGLGVA peptide (10 μg) was injected into the tail vein of subcutaneous HIFko tumor-bearing mice. After 60 min of circulation tumor was excised and prepared for histological analysis. Peptide was visualized by using an antibody against FITC (rabbit anti-FITC, Zymed Laboratories). FIG. 4A. Peptide was not detected in the tumor tissue. FIG. 4B. Same microscopic field as in FIG. 4A. Nuclei were visualized by DAPI staining (blue).

Example 5

Figure 5:
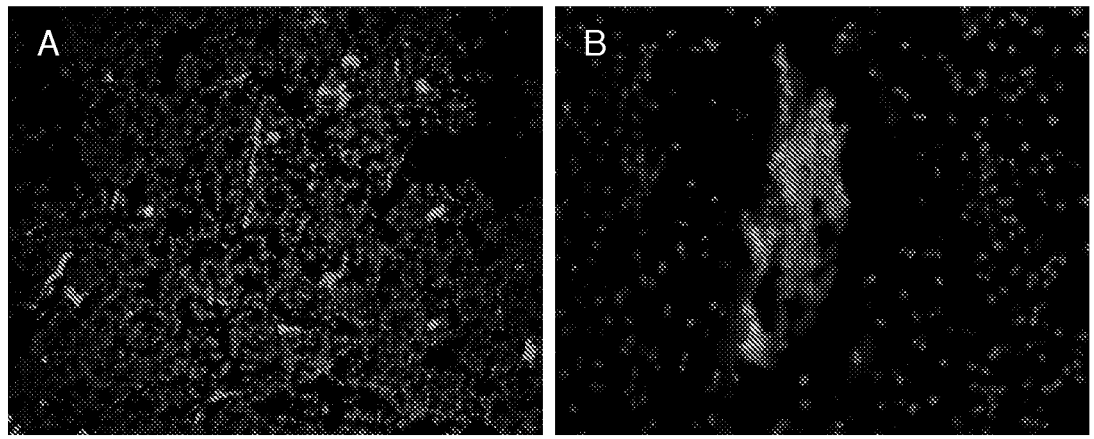
FIG. 5. (A and B) Homing pattern of the fluorescein-conjugated CGLSGLGVA peptide is different in different intracranial tumors.

Homing Pattern of the Fluorescein-Conjugated CGLSGLGVA Peptide is Different in Different Intracranial Tumors Fluorescein-conjugated CGLSGLGVA peptide (10 μg) was injected into tail vein of murine HIFko or human U87MG intracranial xenograft bearing mice. After 60 min of circulation tumor-containing brain was excised and prepared for histological analysis. Peptide was visualized by using an antibody against fluorescein (rabbit anti-FITC, Zymed Laboratories). FIG. 5A: Peptide (red) was detected diffusively in the whole tumor tissue of the HIFko islet tumors while in U87MG tumors peptide distribution resembled that of blood vessels (FIG. 5B). Nuclei were visualized by DAPI staining (blue).

Example 6

Fluorescein-Conjugated CGLSGLGVA Peptide does not Colocalize with the Endothelial Cell Marker PECAM-1

Figure 6:
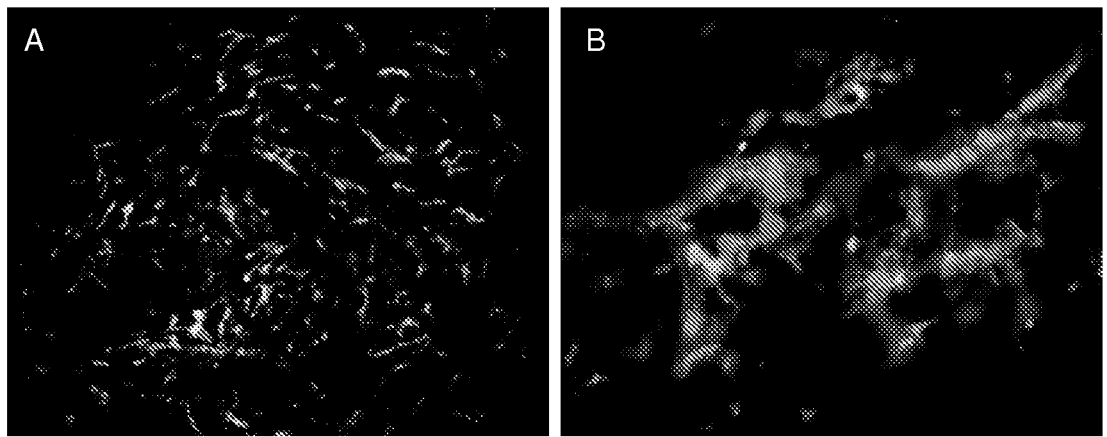
FIG. 6. (A and B) Fluorescein-conjugated CGLSGLGVA peptide does not colocalize with the endothelial marker PECAM-1.

Fluorescein-conjugated CGLSGLGVA peptide (10 μg) was injected into the tail vein of intracranial human U87MG tumor-bearing mice. After 60 min of circulation tumor-containing brain was excised and prepared for histological analysis. Peptide was visualized by using an antibody against fluorescein (rabbit anti-FITC, Zymed Laboratories). FIGS. 6A and 6B: Peptide (red) did not colocalize with the blood vessel marker PECAM-1 (green) (rat anti-mouse PECAM-1, BD Pharmingen) but was found in the close vicinity of blood vessels. Magnification in FIG. 6A, 200×; FIG. 6B, 400×.

REFERENCES

Blouw, B., Song, H., Tihan, T., Bosze, J., Ferrara, N., Gerber, H. P., Johnson, R. S., and Bergers, G. (2003). The hypoxic response of tumors is dependent on their microenvironment. Cancer Cell 4, 133-146.

Hoffman, J. A., Giraudo, E., Singh, M., Zhang, L., Inoue, M., Porkka, K., Hanahan, D., and Ruoslahti, E. (2003). Progressive vascular changes in a transgenic mouse model of squamous cell carcinoma. Cancer Cell 4, 383-391.

Hoffman, J. A., Laakkonen, P., Porkka, K., Bernasconi, M., and Ruoslahti, E. (2004). In vivo and ex vivo selections using phage-displayed libraries. In Phage Display, T. Clackson, and H. B. Lowman, eds. (Oxford, U.K: Oxford University Press), pp. 171-192.

Holash, J., Maisonpierre, P. C., Compton, D., Boland, P., Alexander, C. R., Zagzag, D., Yancopoulos, G. D., and Wiegand, S. J. (1999). Vessel cooption, regression, and growth in tumors mediated by angiopoietins and VEGF. Science 284, 1994-1998.

Joyce, J. A., Laakkonen, P., Bernasconi, M., Bergers, G., Ruoslahti, E., and Hanahan, D. (2003). Stage-specific vascular markers revealed by phage display in a mouse model of pancreatic islet tumorigenesis. Cancer Cell 4, 393-403.

Kim, E. S., Serur, A., Huang, J., Manley, C. A., McCrudden, K. W., Frischer, J. S., Soffer, S. Z., Ring, L., New, T., Zabski, S., et al. (2002). Potent VEGF blockade causes regression of coopted vessels in a model of neuroblastoma. Proc Natl Acad Sci U S A 99, 11399-11404.

Kunkel, P., Ulbricht, U., Bohlen, P., Brockmann, M. A., Fillbrandt, R., Stavrou, D., Westphal, M., and Lamszus, K. (2001). Inhibition of glioma angiogenesis and growth in vivo by systemic treatment with a monoclonal antibody against vascular endothelial growth factor receptor-2. Cancer Research 61, 6624-6628.

Laakkonen, P., Akerman, M. E., Biliran, H., Yang, M., Ferrer, F., Karpanen, T., Hoffman, R. M., and Ruoslahti, E. (2004). Antitumor activity of a homing peptide that targets tumor lymphatics and tumor cells. Proc Natl Acad Sci U S A 101, 9381-9386.

Laakkonen, P., Porkka, K., Hoffman, J. A., and Ruoslahti, E. (2002). A tumor-homing peptide with a targeting specificity related to lymphatic vessels. Nat Med 8, 751-755.

Laakkonen, P., Ruoslahti, E. (2006). Selective Delivery to Vascular Addresses: In Vivo Applications of Cell-Type-Specific Cell-Penetrating Peptides. In Handbook of Cell-Penetrating Peptides, U. Langel, ed. (Taylor & Francis group), pp. 413-422.

Rubenstein, J. L., Kim, J., Ozawa, T., Zhang, M., Westphal, M., Deen, D. F., and Shuman, M. A. (2000). Anti-VEGF antibody treatment of glioblastoma prolongs survival but results in increased vascular cooption. Neoplasia (New York) 2, 306-314.

Ruoslahti, E. (2002). Specialization of tumour vasculature. Nature Reviews Cancer 2, 83-90.

Zhang, L., Giraudo, E., Hoffman, J. A., Hanahan, D., and Ruoslahti, E. (2006). Lymphatic Zip Codes in Premalignant Lesions and Tumors. Cancer Res. 66, 5696-5706.

The invention claimed is:

1. A peptide consisting of the amino acid sequence CGLSGLGVA (SEQ ID NO:1).

2. The peptide according to claim 1 for use in diagnosing an invasive brain cancer or metastatic brain lesions.

3. The peptide according to claim 1 for use in targeting pharmaceutically active agents to invasive brain cancer or metastatic brain lesions.

4. A composition comprising the peptide according to claim 1 in association with at least one carrier and/or diluent.

5. A pharmaceutical composition comprising a pharmaceutically active agent in association with the peptide according to claim 1, and at least one pharmaceutically acceptable carrier and/or diluent.

6. The pharmaceutical composition according to claim 5, wherein the pharmaceutically active agent is a pro-apoptotic peptide or a chemotherapeutic or radiotherapeutic agent.

7. A diagnostic or imaging composition comprising the peptide according to claim 1, and a detectable label.

* * * * *